United States Patent [19]

Havera et al.

[11] 4,230,710
[45] Oct. 28, 1980

[54] AMIDE DERIVATIVES OF 2-SUBSTITUTED ANILINO-HEXAHYDROBENZO[A]-QUINOLIZINES, AND METHODS OF TREATING HYPERTENSION EMPLOYING THEM

[75] Inventors: Herbert J. Havera, Edwardsburg, Mich.; Wallace G. Strycker, Goshen, Ind.

[73] Assignee: Miles Laboratories, Inc., Elkhart, Ind.

[21] Appl. No.: 953,356

[22] Filed: Oct. 23, 1978

[51] Int. Cl.³ .................. A61K 31/47; C07D 455/06
[52] U.S. Cl. ........................................ 424/258; 546/95
[58] Field of Search ........................... 546/95; 424/258

[56] References Cited

U.S. PATENT DOCUMENTS

| 3,635,986 | 1/1972 | Van Dyke, Jr. ................ 546/95 |
| 3,995,041 | 11/1976 | Havera et al. ................ 424/258 |
| 4,076,820 | 2/1978 | Archibald et al. .............. 424/258 |

Primary Examiner—Donald G. Daus
Assistant Examiner—Diana G. Rivers
Attorney, Agent, or Firm—Jerome L. Jeffers

[57] ABSTRACT

Disclosed are novel 2-substituted anilino-hexahydrobenzo[a]quinolizines of the formula:

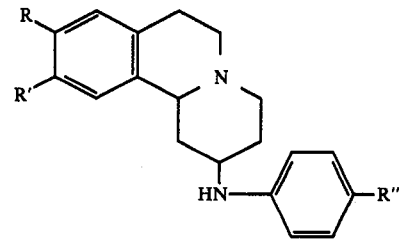

wherein R and R' are independently H or —OCH$_3$ and R" is

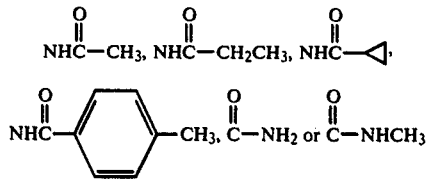

These compounds, and their pharmacologically acceptable, non-toxic acid addition salts are useful as antihypertensive agents. Certain of the compounds disclosed herein elicit this effect without producing concomitant cardiac stimulation.

20 Claims, No Drawings

AMIDE DERIVATIVES OF 2-SUBSTITUTED ANILINO-HEXAHYDROBENZO[A]QUINOLIZINES, AND METHODS OF TREATING HYPERTENSION EMPLOYING THEM

BACKGROUND OF THE INVENTION

U.S. Pat. No. 3,635,986 (issued Jan. 18, 1972) discloses 2-substituted amino-hexahydrobenzo [a] quinolizines of the formula:

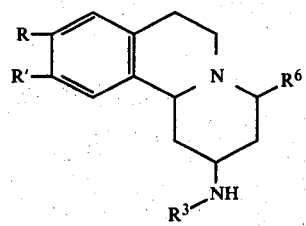

wherein R and R' can be H or O-(lower) alkyl, $R^6$ can be H and $R^3$ can be substituted phenyl. This reference does not disclose substitution of the phenyl ring (when $R^3$ is phenyl) with an amine or amide group.

U.S. Pat. No. 3,995,041 (issued Nov. 30, 1976) discloses derivatives of 2-substituted-hydroxyanilino-hexahydro-2H-benzo [a] quinolizines of the formula:

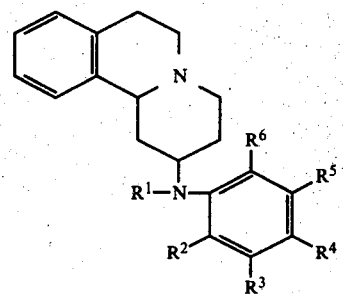

wherein $R^1$ is hydrogen or an alkanoyl group of 2 to 4 carbon atoms and $R^2$, $R^3$, $R^4$, $R^5$ and $R^6$ are hydrogen, hydroxyl or methyl with the proviso that at least one of the $R^2$-$R^6$ groups is hydroxyl.

These prior art compounds are disclosed as having utility as anti-hypertensive agents and coronary dilators respectively.

The compounds of the present invention differ from those of the prior art in that the anilino group in the molecule is p-substituted with an amide group. The compounds of this invention exhibit utility as anti-hypertensive agents. In addition, certain of the compounds disclosed herein, in contrast to prior art compounds of similar chemical structure, exhibit the ability to lower blood pressure without producing tachycardia.

Compounds lowering blood pressure by producing peripheral vasodilatation, such as hydralazine, have found limited use in the treatment of arterial hypertension mainly because their blood pressure effect is accompanied by reflex cardiac stimulation (D. M. Aviado and H. Salem, in New Antihypertensive Drugs, A. Scriabine and C. S. Sweet, eds. Spectrum Publications, New York, 1975. p. 527). Benzoquinolizine derivatives have been reported to decrease blood pressure by this mechanism (J. W. Van Dyke et al. J. Med. Chem. 15:91, 1972). Some of the present compounds elicit this effect without producing concomitant cardiac stimulation, as evidenced by their lack of effect on heart rate.

SUMMARY OF THE INVENTION

The present invention involves 2-substituted anilino-hexahydrobenzo [a] quinolizines of the formula:

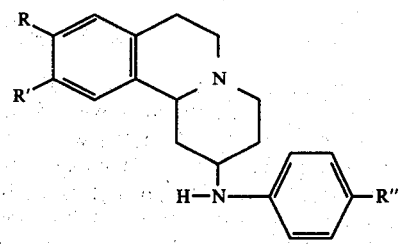

wherein R and R' are independently H or —$OCH_3$ and R" is

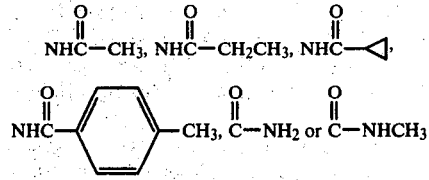

and pharmacologically acceptable, non-toxic acid addition salts thereof.

Also included within the scope of this invention is a method of treating hypertension in an individual requiring such treatment which involves administering to said individual an effective amount of one of the foregoing compounds.

DETAILED DESCRIPTION AND PREFERRED EMBODIMENTS

The compounds of the present invention may be prepared according to the following reaction sequence:

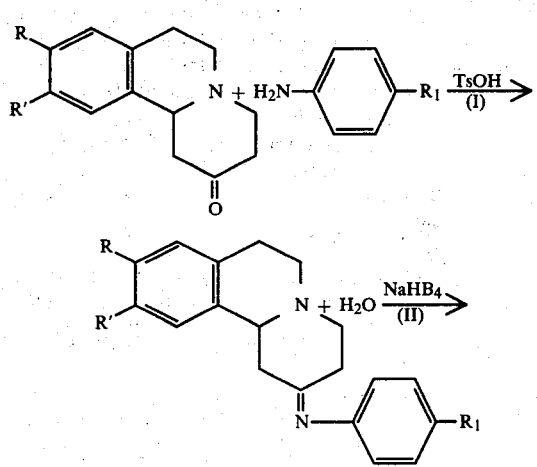

-continued

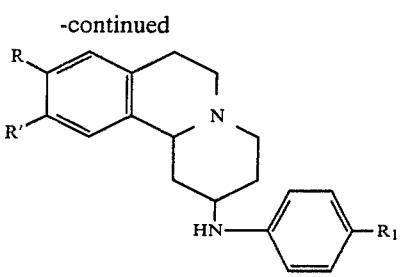

In the above sequence R and R' are defined above, $R_1$ is one of the amide groups defined above and TsOH is toluenesulfonic acid. In step I of the sequence, 2-oxo-1,3,4,6,7,11b-hexahydro-2H-benzo[a] quinolizine is reacted with the appropriate amine to form a Schiff base. The solvent utilized is not critical provided, however, it is not reactive with either the reactants or the products. Suitable solvents include toluene, benzene and xylene. The reaction mixture is advantageously maintained under reflux in the presence of a catalyst such as TsOH to initiate the reaction. Water formed during the reaction is removed in order to drive the reaction to completion. The Schiff base that is formed in step I is then reduced to the corresponding amine in step II by its reaction with $NaBH_4$. Step II is advantageously carried out in a polar solvent such as methanol, ethanol or 2-propanol.

The starting material in the above reaction, 1,3,4,6,7,11b-hexahydro-2oxo-2H-benzo[a]quinolizine, can be prepared by the following reaction sequence:

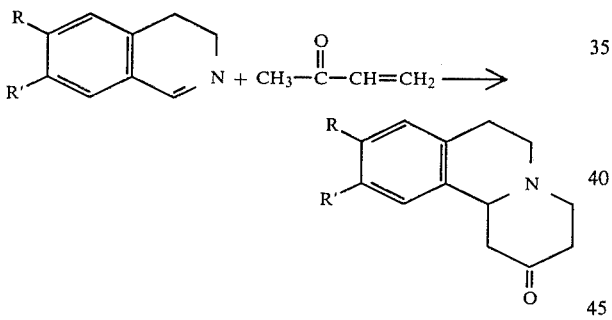

This synthesis is further described by Beke et al. Chem. Ber., 95, 2132–2136 (1962).

Compounds of this invention may be prepared and utilized in the form of the free base. Preferably, however, the compounds are used as pharmacologically acceptable, non-toxic, water soluble addition salts of inorganic or organic acids such as halogen acids, sulfuric acid, maleic acid or the like.

The preparation of the compounds of the present invention is further illustrated by the following examples in which all temperatures are in degrees centigrade.

EXAMPLE I 2-(4-Acetylaminoanilino)-1,3,4,6,7,11b-hexahydro-2H-benzo[a]quinolizine (TR-3429)

A mixture of 1,3,4,6,7,11b-hexahydro-2-oxo-2H-benzo[a]quinolizine (8 g, 0.04 mole; prepared as described by Beke et al), 4-aminoacetanilide (6 g, 0.04 mole), a catalytic amount of p-toluenesulfonic acid (TsOH), 150 ml of toluene and 25 ml of dimethylformamide (DMF) was refluxed for 18 hours with the water produced being collected in a Dean-Stark trap. The solvent was removed in vacuo and the concentrate dissolved in 150 ml of methanol and cooled in an ice bath whereupon 8 g of $NaBH_4$ was added in portions. At this point the mixture was stirred in the cold for 1 hour and at about 18° C. overnight. The solvent was removed in vacuo, the concentrate crystallized from acetone and petroleum ether and recrystallized from benzene and petroleum ether to yield 2 g of the desired product, m.p. 210°–3°.

Anal. Calcd. for $C_{21}H_{25}N_3O$: C, 75.18; H, 7.51; N, 12.53; Found: C, 75.15; H, 7.54; N, 12.58.

EXAMPLE II 2-(4-Acetylaminoanilino)-1,3,4,6,7,11b-hexahydro-9,10-dimethoxy-2H-benzo[a]quinolizine hydrochloride (TR-3605)

A mixture of 1,3,4,6,7,11b-hexahydro-9,10-dimethoxy-2-oxo-2H-benzo[a]quinolizine (10.4 g, 0.04 mole) prepared as described by Beke et al, 4-aminoacetanilide (6.0 g, 0.04 mole), a catalytic amount of TsOH, 25 ml of DMF and 150 ml of benzene was refluxed for 18 hours and the water produced collected in a Dean-Stark trap. The solvent was removed in vacuo to leave an oil which was dissolved in 150 ml of MeOH, cooled in an ice bath and $NaBH_4$ (7 g) was added in portions. The mixture was stirred in the cold for 1 hour and refluxed for 1.5 hours. The solvent was removed in vacuo whereupon water was added and the mixture extracted with chloroform. The chloroform extracts were dried over $MgSO_4$ and concentrated in vacuo to leave the free base as an oil. The free base was converted to the HCl salt with hydrochloric acid in 2-propanol, whereupon the salt was recrystallized from methanol-ether and twice from a mixture of methanol, 2-propanol and ethyl acetate to yield 2.8 g of the desired product, m.p. (decomposes at 270°–1°).

Anal. Calcd for $C_{23}H_{29}N_3O_3.2HCl$: C, 58.97; H, 6.67; N, 8.97; Found: C, 58.21; H, 6.65; N, 9.03.

EXAMPLE III 2-(4-Acetylaminoanilino)-1,3,4,6,7,11b-hexahydro-9-methoxy-2H-benzo[a]quinolizine (TR-3682)

A mixture of 1,3,4,6,7,11b-hexahydro-9-methoxy-2-oxo-2H-benzo[a]quinolizne (7.0 g, 0.030 mole), 4-aminoacetanilide (4.6 g, 0.030 mole), a catalytic amount of TsOH, 100 ml of DMF and 400 ml of toluene was refluxed for 18 hours with the water produced being collected in a Dean Stark trap. The mixture was filtered and concentrated in vacuo whereupon the concentrate was dissolved in 15 ml of MeOH, cooled in an ice bath and 8 g of $NaBH_4$ added in portions. The resulting mixture was stirred in the cold for 2 hours and refluxed for 1 hour whereupon the solvent was removed in vacuo to leave the free base. The free base (6 g) was chromatographed over 500 g of silica gel using benzene-methanol (9:1) as eluant. The major fraction (5 g) was recrystallized from aqueous methanol to yield 2.9 g of the desired product m.p. 219°–21°.

Anal. Calcd for $C_{22}H_{27}N_3O_2$: C, 72.30; H, 7.45; N, 11.50; Found: C, 72.13; H, 7.17; N, 11.44.

EXAMPLE IV 2-(4-Acetylaminoanilino)-1,3,4,6,11b-hexahydro-10-methoxy-2H-benzo[a]quinolizine (TR-3766)

A mixture of 1,3,4,6,7,11b-hexahydro-10-methoxy-2-oxo-2H-benzo[a]quinolizine (6.5 g, 0.028 mole), 4- aminoacetanilide (4.3 g, 0.028 mole), a catalytic amount of TsOH, 30 ml of DMF and 200 ml of toluene was refluxed for 18 hours with the water produced in the reaction being collected in a Dean-Stark trap. The solvent was removed in vacuo to leave a concentrate which was dissolved in 150 ml of 2-propanol. At this point 6 g of NaBH$_4$ was added in portions and the mixture stirred at room temperature for 1 hour and then refluxed for 2 hours. The mixture was diluted with MeOH and concentrated in vacuo whereupon the concentrate was dissolved in water and extracted with chloroform. The chloroform extracts were dried over MgSO$_4$ and concentrated in vacuo whereupon the concentrated material was twice recrystallized from 2-propanol and petroleum ether to yield 1.5 g of the desired product, m.p. 211°–3°.

Anal. Calcd for $C_{22}H_{27}N_3O_2$: C, 72.30; H, 7.45; N, 11.50; Found: C, 71.84; H, 7.20; N, 11.25.

EXAMPLE V 2-(4-Acetylaminoanilino)-1,3,4,6,7,11b-hexahydro-9,10-dimethoxy-2H-benzo[a]quinolizine fumarate (TR-3786)

The free base of the compound prepared in Example II (TR-3605) in the amount of 1 g and 0.6 g of fumaric acid were dissolved in 75 ml of absolute ethanol. The solution was heated to boiled and allowed to cool whereupon the salt was collected and recrystallized from absolute ethanol to yield 1 g of the desired product m.p. (decomposed at 221°–2°).

Anal. Calcd for $C_{23}H_{29}N_3O_2 \cdot \frac{1}{2}C_4H_4O_4$: C, 66.21; H, 6.89; N, 9.27; Found: C, 66.05; H, 6.87; N, 9.00.

EXAMPLE VI 1,3,4,6,7,11b-Hexahydro-9,10-dimethoxy-2[4-(4-methoxybenzoyl amino)anilino]-2H-benzo[a]quinolizine Hydrochloride (TR-3886)

A mixture of 1,3,4,6,7,11b-hexahydro-9,10-dimethoxy-2-oxo-2H-benzo[a]quinolizine (7.8 g, 0.03 mole), 4-amino-4'-methoxy benzanilide (7.3 g, 0.03 mole), a catalytic amount of TsOH, 50 ml of DMF and 150 ml of toluene was refluxed for 18 hours with the water generated by the reaction being collected in a Dean-Stark trap. The solvent was removed in vacuo and the concentrate in 150 ml of methanol was cooled in an ice bath while NaBH$_4$ (8 g) was added in portions. The mixture was stirred in the cold for 1 hour at room temperature and then refluxed for 1 hour. At this point the solvent was removed in vacuo and the remaining concentrate dissolved in water and extracted with CHCl$_3$. The extracts were dried over MgSO$_4$, concentrated in vacuo and chromatographed over 550 g of silica gel using ethyl acetate-methanol (4:1) as eluant. The major fraction (9 g) was converted to the HCl salt with a solution of HCl$_{(g)}$ in a mixture of 2-propanol, methanol and ethyl acetate and the salt was recrystallized from methanol-ethyl acetate to yield 3.6 g of the desired product m.p. (decomposed 265°–7°).

Anal. Calcd for $C_{29}H_{33}N_3O_4 \cdot 2HCl$: C, 62.15; H, 6.29; N, 7.50; Found: C, 62.02; H, 6.22; N, 7.52.

EXAMPLE VII 2-(4-Benzoylaminoanilino)-1,3,4,6,7,11b-hexahydro-9,10-dimethoxy-2H-benzo[a]quinolizine hydrochloride (TR-3887)

A mixture of 1,3,4,6,7,11b-hexahydro-9,10-dimethoxy-2-oxo-2H-benzo[a]quinolizine (7.8 g, 0.03 mole), 4-amino-benzanilide (6.4 g, 0.03 mole), a catalytic amount of TsOH, 50 ml of DMF and 150 ml of toluene was refluxed for 5 days with the water produced being collected in a Dean-Stark trap. The solvent was removed in vacuo and the concentrated residue dissolved in 150 ml of methanol and cooled in an ice bath whereupon 8 g of NaBH$_4$ was added in portions. This mixture was stirred in the cold for 1 hour and refluxed for 1 hour whereupon the solvent was removed in vacuo and the concentrated residue suspended in water and extracted with chloroform. The extract was dried over MgSO$_4$, concentrated in vacuo and the residue chromatographed on 550 g of silica gel using ethyl acetate-methanol (4:1) as eluant. The major fraction (5.8 g) was converted to the HCl salt by addition of hydrogen chloride dissolved in a mixture of 2-propanol, methanol and ethyl acetate. The salt was recrystallized from methanol-ethyl acetate to yield 3.0 g of the desired product, m.p. (decomposed at 287°–8°).

Anal. Calcd for $C_{28}H_{31}N_3O_3 \cdot 2HCl$: C, 63.40; H, 6.27; N, 7.92; Found: C, 63.09; H, 6.29; N, 7.89.

EXAMPLE VIII 1,3,4,6,7,11b-Hexahydro-9,10-dimethoxy-2-(4-propanoylaminoanilino)-2H-benzo[a]quinolizine Hydrochloride (TR-3891)

A mixture of 1,3,4,6,7,11b-hexahydro-9,10-dimethoxy-2-oxo-2H-benzo[a]quinolizine (10 g, 0.038 mole), 4-aminopropionanilide (6.4 g, 0.038 mole), a catalytic amount of TsOH, 50 ml of DMF and 150 ml of toluene was refluxed for 18 hours and the water produced was collected in a Dean-Stark trap. The solvent was removed in vacuo and the concentrated residue was suspended in 150 ml of methanol, cooled in ice bath whereupon 8 g of NaBH$_4$ was added in portions. The mixture was stirred in the cold for 1 hour, refluxed for 1 hour and concentrated in vacuo. The concentrated material was suspended in water and extracted with CHCl$_3$. The extract was dried over MgSO$_4$, concentrated in vacuo and chromatographed over silica gel using ethyl acetate-methanol (3:1) as eluant. The major fraction (6.8 g) was converted to the HCl salt with hydrogen chloride in a mixture of 2-propanol, methanol and ethyl acetate and twice recrystallized from methanol-ethyl acetate to yield 2.9 g of the desired product m.p. (decomposed at 289°–91°).

Anal. Calcd for $C_{24}H_{31}N_3O_3 \cdot 2HCl$: C, 59.74; H, 6.89; N, 8.71; Found: C, 59.18; H, 6.79; N, 8.58.

EXAMPLE IX 2-(4-Cyclopropylcarboxylamino)anilino-1,3,4,6,7,11b-hexahydro-9,10-dimethoxy-2H-benzo[a]quinolizine Hydrochloride (TR-3901)

A mixture of 1,3,4,6,7,11b-hexahydro-9,10-dimethoxy-2-oxo-2H-benzo[a]quinolizine (8.5 g, 0.032 mole), 4-cyclopropyl-carboxylaminoaniline (6.5 g, 0.037 mole), a catalytic amount of TsOH, 50 ml of DMF and 125 ml of toluene was refluxed for 18 hours and the water produced collected in a Dean-Stark trap. The solvent was removed in vacuo and the concentrate dissolved in 150 ml of methanol and cooled in an ice bath whereupon 8 g of NaBH$_4$ was added in portions. The mixture was stirred in the cold for 1 hour, refluxed for 1 hour and the solvent removed in vacuo. The concentrate was dissolved in water and extracted with chloroform, the extracts dried over MgSO$_4$, concentrated in vacuo and the concentrate chromatographed over silica gel using ethyl acetate-methanol (3:1) as eluant. The major fraction (5.6 g) was converted to the HCl salt with hydrogen chloride dissolved in a mixture of 2-propanol, methanol and ethyl acetate and recrystallized once from 2-propanol and twice from methanol-ethyl acetate to yield 2.6 g of the desired product m.p. (decomposed at 264°–5°).

Anal. Calcd for $C_{25}H_{31}N_3O_3 \cdot 2HCl$: C, 60.72; H, 6.73; N, 8.50; Found: C, 60.68; H, 6.74; N, 8.56.

EXAMPLE X 1,3,4,6,7,11b-Hexahydro-9,10-dimethoxy-2-[4-(4-methylbenzoylamino)anilino]-2H-benzo[a]quinolizine Hydrochloride (TR-3904)

A mixture of 1,3,4,6,7,11b-hexahydro-9,10-dimethoxy-2-oxo-2H-benzo[a]quinolizine-2-one (8.5 g, 0.033 mole), 4-(4-methylbenzoylamino)aniline (7.5 g), a catalytic amount of TsOH, 50 ml of DMF and 100 ml of toluene was refluxed for 18 hours with the water produced being collected in a Dean-Stark trap. The solvent was removed in vacuo whereupon the concentrate was dissolved in water, extracted with chloroform, dried over $MgSO_4$, concentrated in vacuo and chromatographed over silica gel using ethyl acetate-methanol (4:1) as eluant. The major fraction (7.4 g) was converted to the HCl salt with hydrogen chloride dissolved in a mixture of 2-propanol, methanol, and ethyl acetate and twice recrystallized from methanol-ethyl acetate to yield 3.6 g of the desired product, m.p. (decomposed at 253°–5°).

Anal. Calcd for $C_{29}H_{33}N_3O_3 \cdot 2HCl$: C, 63.97; H, 6.48; N, 7.72; Found: C, 63.54; H, 6.49; N, 7.72.

EXAMPLE XI 2-(4-Carbamylanilino)-1,3,4,6,7,11b-hexahydro-9,10-dimethoxy-2H-benzo[a]-quinolizine hydrochloride (TR-3911)

A mixture of 1,3,4,6,7,11b-hexahydro-9,10-dimethoxy-2-oxo-2H-benzo[a]quinolizine (9 g, 0.034 mole), 4-aminobenzamide (5 g), a catalytic amount of TsOH, 50 ml of DMF and 100 ml of toluene was refluxed for 18 hours with the water produced being collected in a Dean-Stark trap. The solvent was removed in vacuo whereupon the concentrate was dissolved in 150 ml of methanol and cooled in an ice bath while 8 g of $NaBH_4$ were added in portions. The resulting mixture was stirred in the cold for 1 hour, refluxed for 1 hour, concentrated in vacuo and the concentrate chromatographed over silica gel using a mixture of ethyl acetate, methanol and chloroform (3:1:1) as eluant. The major fraction (5.2 g) was converted to the HCl salt with hydrogen chloride in a mixture of 2-propanol and ethyl acetate and recrystallized three times from methanol-ethyl acetate to yield 1.1 g of the desired product, m.p. (decomposed at 228°–31°).

Anal. Calcd for $C_{22}H_{27}N_3O_3 \cdot 2HCl$: C, 58.15; H, 6.43; N, 9.25; Found: C, 57.97; H, 6.57; N, 9.13.

EXAMPLE XII 1,3,4,6,7,11b-Hexahydro-9,10-dimethoxy-2-(4-N-methylcarbamyl)anilino-2H-benzo[a]quinolizine (TR-3991)

A mixture of 1,3,4,6,7,11b-hexahydro-9,10-dimethoxy-2-oxo-2H-benzo[a]quinolizine (8.7 g, 0.033 mole), 4-amino-N-methylbenzamide (6.5 g), a catalytic amount of TsOH, 250 ml of toluene and 30 ml of DMF was refluxed for 4 days with the water produced being collected in a Dean-Stark trap. The solvent was removed in vacuo whereupon the concentrate was dissolved in 150 ml of methanol, and cooled in an ice bath while 8 g of $NaBH_4$ was added in portions. The mixture was stirred in the cold for 1 hour and refluxed for 1 hour. At this point the solvent was removed in vacuo and the concentrate dissolved in water, extracted with chloroform, dried over $MgSO_4$ and concentrated. The concentrate was chromatographed over alumina using chloroform-acetone (9:1) as eluant to yield 9 g of product. The product was rechromatographed on silica gel using chloroform-methanol (9:1) as eluant. The 5.5 g of product was crystallized from 2-propanol/petroleum ether to yield 2.9 g of the desired product, m.p. 177°–9°.

Anal. Calcd for $C_{23}H_{29}N_3O_3$: C, 69.85; H, 7.39; N, 10.62; Found: C, 69.12; H, 7.36; N, 10.59.

EXAMPLE XIII

Determination of the anti-hypertensive effects of the compounds of this invention Antihypertensive activity was determined in rats and dogs. Rats were made hypertensive by applying a figure of eight ligature to one kidney and removing the contralateral kidney two weeks later. At least four weeks after the second operation the animals were subjected to indirect systolic blood pressure measurements with an occluding cuff and pulse sensor system applied to the tail. Pressure measurements were made before and 1, 2, 4, 6 and 8 hours after oral administration of the test compounds at a dose of 31 mg/kg. Each compound was tested in 5 or 10 rats. Statistical significance of differences between control and post treatment values was determined by Wilcoxon's signed rank test (F. Wilcoxon and R. A. Wilcox, Some Rapid Approximate Statistical Procedures, Lederle Laboratories, Pearl River, 1964). The results of this study are presented in Table I. Compounds significantly lowering blood pressure in rats were subsequently tested in dogs made hypertensive by unilateral renal artery constriction and contralateral nephrectomy. Systolic and diastolic blood pressures were determined indirectly with an occluding cuff and pulse sensor system applied to the tail of the animals. The resultant arterial pulsations were inscribed in a suitable recorder and were counted to determine heart rate. Mean blood pressure was calculated by adding ⅓ of the differential pressure (systolic minus diastolic) to the diastolic pressure. Pressure and heart rate measurements were made before and 1, 2, 4, 6 and 8 hours after oral administration of the test compounds at a dose of 10 mg/kg. All compounds were tested in one dog; those decreasing blood pressure without increasing heart rate were tested in additional animals. The results of this study are presented in Table II.

TABLE I

Antihypertensive Activity of Amine and
Amide Benzoquinolizines in the Rat-Test Dose: 31 mg/kg

| Ex. No. | TR | Number of Rats | Initial BP, mmHg | Change in Systolic Blood Pressure, mmHg, at | | | | |
|---|---|---|---|---|---|---|---|---|
| | | | | 1 hr | 2 hr | 4 hr | 6 hr | 8 hr |
| 1 | 3429** | 10 | 213 | −101* | −106* | −87* | −72* | −52* |
| 2 | 3605 | 10 | 190 | −74* | −65* | −58* | −42* | −38* |
| 3 | 3682** | 10 | 182 | −88* | −88* | −78* | −61* | −44* |
| 4 | 3766 | 10 | 196 | −72* | −54* | −34* | −12 | +2 |
| 5 | 3786 | 10 | 187 | −60* | −61* | −54* | −48* | −37* |
| 6 | 3886 | 5 | 204 | −6 | +4 | +13 | +8 | +10 |
| 7 | 3887 | 10 | 200 | −8 | −12 | +2 | +2 | 0 |
| 8 | 3891 | 10 | 204 | −40* | −39* | −34* | −21* | −5 |
| 9 | 3901 | 10 | 187 | −69* | −63* | −63* | −42* | −17* |
| 10 | 3904 | 10 | 185 | −29* | −31* | −17* | −12 | 0 |
| 11 | 3911 | 10 | 189 | −73* | −59* | −48* | −35* | −18* |
| 12 | 3991 | 10 | 206 | −51* | −63* | −51* | −35* | −16* |

\* = Statistically significant change from control.
\*\* = Tested at 10 mg/kg. Death was observed at 31 mg/kg.

From Table I, it can be determined that not all of the 2-substituted anilinohexahydrobenzo[a]quinolizines prepared by the foregoing procedure are effective as antihypertensive agents since TR-3886 where R" is

and TR-3887 where R" is were not active in the rat test.

In the dog test, both blood pressure and heart rate were measured after administration of the compound. In general, the criterion for useful activity in this test is a decrease in blood pressure without substantially increasing the heart rate. Applying a criterion of a decrease in blood pressure of at least 10 mmHg and rise in heart rate no greater than 30 beats per minute results in TR-3605, TR-3786, TR-3891, TR-3904 and TR-3911 meeting this standard. None of the prior art compounds meet this criterion which indicates that those which do possess the therapeutically meaningful advantage of eliciting less tachycardia than the prior art compounds.

Several compounds, i.e., TR-3904, TR-3786 and TR-3911, meet the more rigorous standard of decreasing blood pressure by at least 20 mmHg and increasing heart rate by less than 20 beats per minute which represents a clear advantage over the prior art compounds.

TABLE II

Antihypertensive and Heart Rate Effects
of Amine and Amide Benzoquinolizines in the Dog.
Test Dose: 10 mg/kg.

| Ex. No. | TR | Number of Dogs | Parameter | Initial Value | Change in Parameter at | | | | |
|---|---|---|---|---|---|---|---|---|---|
| | | | | | 1 hr | 2 hr | 4 hr | 6 hr | 8 hr |
| 1 | 3429** | 1 | MBP,mmHg | 125 | +1 | −12 | −5 | +5 | +33 |
| | | | HR, b/min | 112 | −16 | +44 | +32 | +30 | +28 |
| | | | HR | 104 | +12 | +36 | +56 | +16 | +12 |
| 2 | 3605 | 6 | MBP | 140 | −16 | −15 | −7 | −7 | −6 |
| | | | HR | 87 | +18 | +22 | +21 | +17 | +8 |
| 3 | 3682 | 1 | MBP | 123 | −4 | −31 | −26 | −3 | −12 |
| | | | HR | 80 | +16 | +48 | +48 | +40 | +40 |
| 4 | 3766 | 1 | MBP | 134 | −30 | −10 | +7 | −1 | 0 |
| | | | HR | 76 | −4 | +20 | +44 | +28 | +32 |
| 5 | 3786 | 6 | MBP | 142 | −27 | −42 | −28 | −20 | −3 |
| | | | HR | 89 | +15 | +22 | +22 | +16 | +5 |
| 8 | 3891 | 1 | MBP | 138 | −31 | +5 | +5 | +4 | +2 |
| | | | HR | 76 | −12 | +12 | +12 | | 0 |
| 9 | 3901 | 1 | MBP | 137 | −4 | −18 | +4 | −4 | −6 |
| | | | HR | 60 | 0 | 0 | +12 | +16 | +4 |
| 10 | 3904 | 3 | MBP | 137 | −13 | −7 | −18 | −22 | −9 |
| | | | HR | 83 | +5 | −3 | +8 | +5 | +12 |
| 11 | 3911 | 3 | MBP | 140 | −10 | −25 | −26 | −21 | −13 |
| | | | HR | 92 | +9 | +29 | +19 | +20 | +17 |
| 12 | 3991 | 1 | MBP | 156 | −18 | −95 | −22 | −6 | −6 |
| | | | HR | 108 | +68 | +96 | +44 | +36 | +20 |

\*\* = Tested at 3.1 mg/kg.

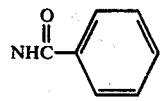

Several prior art compounds having structural similarity to those of the present invention were tested for their antihypertensive activity in the rat by the procedure set out above. The results of these tests for compounds having the general formula

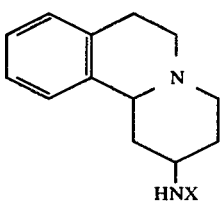

are set out in Table III. Those compounds which were found to be active in the rat test were tested on the dog as previously described. The results of testing in the dog are set out in Table IV.

TABLE III

Antihypertensive Activity of Prior Art Benzoquinolizines in the Rat. Test Dose: 31mg/kg, p.o.

| TR | X | Number of Rats | Initial BP,mmHg | 1 hr | 2 hr | 4 hr | 6 hr | 8 hr |
|---|---|---|---|---|---|---|---|---|
| 2343 | 3,4,5-(H₃CO)₃-phenyl | 5 | 213 | +2 | +5 | −6 | −4 | +1 |
| 2354 | 3,4-Cl₂-phenyl | 10 | 194 | −23 | −24 | −11 | −11 | 0 |
| 2420 | 3,4-(H₃CO)₂-phenyl | 10 | 195 | −19 | −18 | 0 | −10 | −12 |
| 2425 | 4-H₃C-phenyl | 10 | 202 | −34 | −32 | −34 | −12 | −2 |
| 2577 | 4-H₃CO-phenyl | 10 | 199 | −28 | −34 | −24 | −25 | −26 |
| 3273 | 4-OH-phenyl | 5 | — | −36 | −24 | −22 | −27 | −14 |
| 3324 | 2-OH-phenyl | 5 | — | −10 | −8 | +4 | +4 | +4 |

TABLE IV

Antihypertensive and Heart Rate Effects of Prior Art Benzoquinolizines in the Dog. Test Dose: 10 mg/kg. p.o.

| TR | Number of Dogs | Parameter | Initial Value | 1 hr | 2 hr | 4 hr | 6 hr | 8 hr |
|---|---|---|---|---|---|---|---|---|
| 2354 | 1 | MBP, mmHg | 159 | +6 | 0 | −5 | −1 | 0 |
|  |  | HR, b/min | 112 | −8 | −4 | −4 | +12 | +12 |
| 2420 | 1 | MBP | 133 | −37 | −17 | +11 | +1 | −6 |
|  |  | HR | 92 | −8 | +20 | +48 | +56 | +24 |
| 2425 | 1 | MBP | 150 | −8 | +1 | −1 | +4 | 0 |
|  |  | HR | 112 | −8 | +12 | +44 | +48 | +40 |
| 2577 | 1 | MBP | 113 | +4 | −9 | +5 | +39 | +36 |
|  |  | HR | 124 | +36 | +44 | +48 | +44 | +36 |
| 3273 | 3 | MBP | 119 | −19 | −8 | +9 | +15 | +5 |
|  |  | HR | 99 | +41 | +44 | +29 | +10 | +4 |

From Table IV it can be determined that none of the prior art compounds which were active in the rat test were active in the dog test as determined by the previously referred to criterion.

Administration of the compounds of the present invention by conventional means produces a lowering of blood pressure in hypertensive individuals. Certain of the compounds relieve hypertension without causing a substantial increase in heart rate. Medications prepared with the compounds of the present invention as active ingredients are readily formulated by mixing the compounds in dosage units with fillers, carriers, extenders and/or excipients generally used in preparing pharmaceutical formulations. When mixed in such a formulation, the compound may be in the form of a free base but is preferably in the form of a pharmacologically acceptable non-toxic acid addition salt. The medication may be either in solid or liquid form and may be compounded as tablets, powders, capsules, suspensions and similar dosage forms according to accepted manufacturing methods. These medications may be administered, for example, orally or subcutaneously, in conformity with recognized pharmacological techniques.

What is claimed is:

1. 2-substituted anilino-hexahydrobenzo[a]quinolizines of the formula:

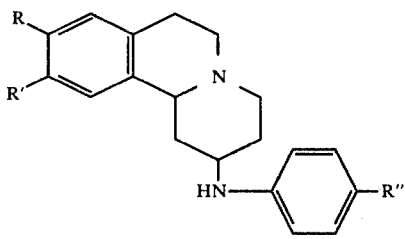

wherein R and R′ are independently H or OCH₃ and R″ is

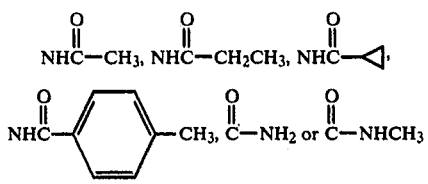

and pharmacologically acceptable, non-toxic acid addition salts thereof.

2. A compound as defined by claim 1 wherein R and R' are H and R" is

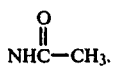

3. A compound as defined by claim 1 wherein R and R' are OCH₃ and R" is

4. The fumaric acid addition salt of the compound of claim 3.

5. A compound as defined by claim 1 wherein R is H, R' is OCH₃ and R" is

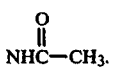

6. A compound as defined by claim 1 wherein R is OCH₃, R' is H and R" is

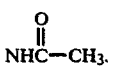

7. A compound as defined by claim 1 wherein R and R' are OCH₃ and R" is

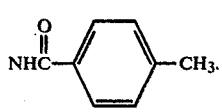

8. The hydrochloric acid addition salt of the compound defined in claim 7.

9. A compound as defined by claim 1 wherein R and R' are OCH₃ and R" is

10. A compound as defined by claim 1 wherein R and R' are OCH₃ and R" is

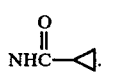

11. A compound as defined by claim 1 wherein R and R' are OCH₃ and R" is

12. The hydrochloric acid addition salt of the compound defined in claim 11.

13. A compound as defined by claim 1 wherein R and R' are OCH₃ and R" is

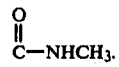

14. A method of treating hypertension in an individual requiring such treatment which method comprises administering to said individual an effective amount of a compound of the formula:

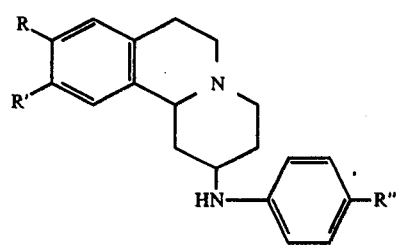

wherein R and R' are independently H or OCH₃ and R" is

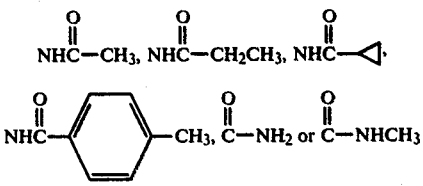

15. The method of claim 14 wherein R and R' are OCH₃ and R" is

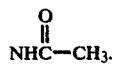

16. The method of claim 15 wherein the compound used is the fumaric acid addition salt of the compound whose use is claimed therein.

17. The method of claim 14 wherein R and R' are OCH₃ and R" is

18. The method of claim 17 wherein the compound used is the hydrochloric acid addition salt of the compound whose use is claimed therein.

19. The method of claim 14 wherein R and R' are OCH₃ and R" is

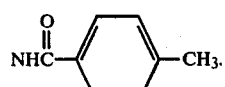

20. The method of claim 19 wherein the compound used is the hydrochloric acid addition salt of the compound whose use is claimed therein.

* * * * *